United States Patent
DuBourdieu et al.

(10) Patent No.: US 10,406,232 B2
(45) Date of Patent: Sep. 10, 2019

(54) ORAL DELIVERY COMPOSITIONS FOR TREATING DERMATITIS DISORDERS IN MAMMALS

(71) Applicant: Vets Plus, Inc., Limerick, ME (US)

(72) Inventors: Daniel J. DuBourdieu, Limerick, ME (US); Rajiv Lall, Menomonie, WI (US); Ajay Srivastava, Menomonie, WI (US)

(73) Assignee: VETS PLUS, INC., Menomonie, WI (US)

( * ) Notice: Subject to any disclaimer, the term of this patent is extended or adjusted under 35 U.S.C. 154(b) by 254 days.

(21) Appl. No.: 14/753,891

(22) Filed: Jun. 29, 2015

(65) Prior Publication Data

US 2016/0374940 A1    Dec. 29, 2016

(51) Int. Cl.

| | | |
|---|---|---|
| A61K 31/02 | (2006.01) | |
| A61K 31/07 | (2006.01) | |
| A61K 31/201 | (2006.01) | |
| A61K 31/341 | (2006.01) | |
| A61K 31/343 | (2006.01) | |
| A61K 31/675 | (2006.01) | |
| A61K 31/7028 | (2006.01) | |
| A61K 47/10 | (2017.01) | |
| A61K 36/484 | (2006.01) | |
| A61K 33/30 | (2006.01) | |
| A61K 47/44 | (2017.01) | |
| A61K 36/9068 | (2006.01) | |
| A61K 36/185 | (2006.01) | |
| A23K 10/30 | (2016.01) | |
| A23K 20/174 | (2016.01) | |
| A23K 20/111 | (2016.01) | |
| A23K 20/158 | (2016.01) | |
| A23K 20/163 | (2016.01) | |
| A23K 20/10 | (2016.01) | |
| A23K 20/20 | (2016.01) | |
| A23K 50/42 | (2016.01) | |
| A23K 40/25 | (2016.01) | |
| A61K 45/06 | (2006.01) | |
| A61K 31/164 | (2006.01) | |
| A61K 31/202 | (2006.01) | |
| A61K 31/375 | (2006.01) | |
| A61K 31/714 | (2006.01) | |
| A23K 20/00 | (2016.01) | |
| A23K 20/105 | (2016.01) | |
| A23K 50/40 | (2016.01) | |
| A61K 47/14 | (2017.01) | |
| A61K 47/22 | (2006.01) | |
| A61K 47/26 | (2006.01) | |
| A61K 47/46 | (2006.01) | |
| A61K 9/14 | (2006.01) | |

(52) U.S. Cl.
CPC .............. *A61K 47/10* (2013.01); *A23K 10/30* (2016.05); *A23K 20/00* (2016.05); *A23K 20/10* (2016.05); *A23K 20/105* (2016.05); *A23K 20/111* (2016.05); *A23K 20/158* (2016.05); *A23K 20/163* (2016.05); *A23K 20/174* (2016.05); *A23K 20/30* (2016.05); *A23K 40/25* (2016.05); *A23K 50/40* (2016.05); *A23K 50/42* (2016.05); *A61K 9/141* (2013.01); *A61K 31/07* (2013.01); *A61K 31/164* (2013.01); *A61K 31/202* (2013.01); *A61K 31/375* (2013.01); *A61K 31/714* (2013.01); *A61K 33/30* (2013.01); *A61K 36/185* (2013.01); *A61K 36/484* (2013.01); *A61K 36/9068* (2013.01); *A61K 45/06* (2013.01); *A61K 47/14* (2013.01); *A61K 47/22* (2013.01); *A61K 47/26* (2013.01); *A61K 47/44* (2013.01); *A61K 47/46* (2013.01)

(58) Field of Classification Search
None
See application file for complete search history.

(56) References Cited

U.S. PATENT DOCUMENTS

| | | | |
|---|---|---|---|
| 7,462,739 B2 | 12/2008 | Park et al. | |
| 2005/0196461 A1 | 9/2005 | Udell | |
| 2005/0214241 A1* | 9/2005 | Kandil | ............... A61K 8/67 424/74 |
| 2006/0029643 A1* | 2/2006 | Ishikawa | ............... A61K 8/375 424/439 |
| 2012/0225936 A1* | 9/2012 | Steward | ............... A61K 31/365 514/468 |
| 2012/0244234 A1* | 9/2012 | Etheve | ............... A61K 9/0095 424/725 |

(Continued)

FOREIGN PATENT DOCUMENTS

EP    0678247 A1 * 10/1995    ........... A23K 20/158

OTHER PUBLICATIONS

Ziegler, Purified Rodent Diet AIN-76A, accessed at http://www.zeiglerfeed.com/Literature/Purified%20Rodent%20Diet%20AIN-76A.pdf on Jan. 3, 2017.*

(Continued)

*Primary Examiner* — Zohreh A Fay
(74) *Attorney, Agent, or Firm* — Daniel A. Blasiole; Charles S. Sara; DeWitt LLP

(57) ABSTRACT

A composition for treating atopic dermatitis in animals containing active compositions of ceramides for skin barrier protection, omega 3 and omega 6 fatty acids for reducing pruritus and botanical extracts for inhibiting 5-lipoxygenase activity, histamine release while modulating the immune system. The active compositions are placed in a soft dough oral delivery system.

2 Claims, No Drawings

(56) References Cited

U.S. PATENT DOCUMENTS

| | | | | |
|---|---|---|---|---|
| 2013/0171204 A1* | 7/2013 | DuBourdieu | ........ | A61K 9/0056 424/400 |
| 2013/0295271 A1* | 11/2013 | Ueda | ........................ | A23G 3/46 426/648 |

OTHER PUBLICATIONS

Zambiazi et al., Curitiba, 25: 111-120 (2007).*
Ohnishi et al., Agricultural and Biological Chemistry, 49: 3609-3611 (1985).*
Peterman et al., Plant Physiol., 71: 55-58 (1983).*
Zhang et al., Planta Med, 73: 336-340 (2007).*
MEG-3 30 powder, DSM, https://www.dsm.com/markets/foodandbeverages/en_US/products/nutritional-lipids/meg-3.html, accessed May 24, 2017.*
Hassanien et al., J. Food Sci Tech, 52: 6136-6142 (2015, epub. Mar. 27, 2015).*
Tou et al., manuscript accessed at https://ntrs.nasa.gov/archive/nasa/casi.ntrs.nasa.gov /20030065983.pdf on May 24, 2017.*
El-Dakhakhny M., et al., "Nigella sativa oil, nigellone and derived thymoquinone inhibit synthesis of 5-lipoxygenase products in polymorphonuclear leukocytes from rats," Journal of Ethnopharmacology, 81, 161-164, 2002.
Grzanna R, et al., "Ginger—an herbal medicinal product with broad anti-inflammatory actions," J Med Food. 8:125-32, 2005, abstract only.
Ji-Young Jung, et al., "Clinical use of a ceramide-based moisturizer for treating dogs with atopic dermatitis," Vet. Sci. (2013), 14(2), 199-205.
Kimata H., "Improvement of atopic dermatitis and reduction of skin allergic responses by oral intake of konjac ceramide," Pediatr Dermatol. Jul.-Aug. 2006; 23(4):386-9.
Kobayashi H, et al., "Diet and Japanese herbal medicine for recalcitrant atopic dermatitis: efficacy and safety," Drugs Exp Clin Res. 30:197-202, 2004, abstract only.
Kumarv P., et al., "Role of Micro-Nutrients in Dermatological Disorders of Dog," INTAS POLIVET (2007) vol. 8 No. II : 467-471, abstract only.
Loga D. et al., "Double blinded crossover study with marine oil supplementation containing high dose eicosapentaenoic acid for the treatment of canin pruritic skin disease," Vet. Dermatology 5:99-104, 1994.
Marsella R, et al., "Investigations on the Effects of a Topical Ceramides—Containing Emulsion (Allerderm Spot on) on Clinical Signs and Skin Barrier Function in Dogs with Topic Dermatitis: a Double-Blinded, Randomized, Controlled Study," Intern J Appl Res Vet Med, vol. 11, No. 2, 2013, abstract only.
Meuller R.S., et. al. "Effect of omega-3 fatty acids on canine atopic dermatitis," Journal of Small Animal Practice. 45, 293-297, 2004, abstract only.
Osamu Ueda, et al., "Distribution in Skin of Ceramide after Oral Administration to Rats," Drug Metab. Pharmacokinet. 24 (2): 180-184 (2009).
Popa I., et al., "Analysis of epidermal lipids in normal and atopic dogs, before and after administration of an oral omega-6/omega-3 fatty acid feed supplement. A pilot study," Veterinary Research Communications, 2011, 35, 8, pp. 501-509, abstract only.
Reiter L.V., et al., "Characterization and quantification of ceramides in the nonlesional skin of canine patients with atopic dermatitis compared with controls," Vet Dermatol. Aug. 2009; 20(4):260-6.
Rosanna Marsella, "An update on the treatment of canine atopic dermatitis," Veterinary Medicine: Research and Reports 2012:3 85-91, abstract only.
Rubin P., et al., "Pharmacotherapy of diseases mediated by 5-lipoxygenase pathway eicosanoids," Prostaglandins Other Lipid Mediat. 83.188-97, 2007, abstract only.
Saeedi M., et al., "The treatment of atopic dermatitis with licorice gel," Journal of Dermatological Treatment 14, 153-157, 2003, abstract only.
Scarff D. H.; et al., "Double blind, placebo-controlled, crossover study of evening primrose oil in the treatment of canine atopy," Veterinary Record, 1992, 131, 5, pp. 97-99, abstract only.
Sharrif Moghaddasi M., "Nigella Sativa Traditional Usages (Black Seed)," Advances in Environmental Biology, 5: 5-16, 2011.
Shirakura et al., "4,8-Sphingadienine and 4-hydroxy-8-sphingenine activate ceramide production in the skin," Lipids in Health and Disease 2012, 11:108.
Subhuti Dharmananda, "Reducing Inflammation with diet and supplements: The Story of Eicosanoid Inhibition," Institute for Traditional Medicine, Portland, Oregon. General Review. 2003.
Supinya Tewtrakul et al., "Anti-allergic activity of some selected plants in the Zingiberaceae family," Journal of Ethnopharmacology 109: 535-538, 2007, abstract only.
Tsuji K, et al., "Dietary glucosylceramide improves skin barrier function in hairless mice," J Dermatol Sci Nov. 2006; 44(2):101-7, abstract only.
Williams RR, et al., "Diagnosing heterozygous familial hypercholesterolemia using new practical criteria validated by molecular genetics," Am J Cardiol. 1993;72:171-6, abstract only.
Yong-Wook Shin, et al, "In-vitro and in-vivo anti-allergenic effects of Glycyrrhiza glabra and its components," Planta Medica 73: 257, 2007, abstract only.
Yoshii, H., et al., "Oxidation stability of eicosapentaenoic and docosahexaenoic acid included in cyclodextrins," Journal of inclusion phenomena and molecular recognition in chemistry 1996, vol. 25, Issue 1-3, pp. 217-220, abstract only.
Yan Zhang et al., "Triptolide Inhibits IL-12/IL-23 Expression in APCs via CCAAT/Enhancer-Binding Protein α," J Immunol. Apr. 1, 2010; 184(7): 3866-3877.
Onuma, M. et al, "A case of canine atopic dermatitis administered with oral glucosylceramide supplementation," Jpn J Vet Dermatol (2008) 14:81-83.
Paterson, S., "Additive benefits of EFAs in dogs with atopic dermatitis after partial response to antihistamine therapy," Journal of Small Animal Practice (1995) 36389-394.
Uchiyama, Taro et al., "Oral intake of glucosylceramide improves relatively higher level of transepidermal water loss in mice and healthy human subjects," Jr. of Health Science (2008) 54(5):559-566.

* cited by examiner

ORAL DELIVERY COMPOSITIONS FOR TREATING DERMATITIS DISORDERS IN MAMMALS

BIBLIOGRAPHY

Complete bibliographical citations to the documents cited herein can be found in the Bibliography immediately preceding the claims.

FIELD OF THE INVENTION

The present invention relates to treatment of dermal disorders in mammals using a soft food delivery system for the active ingredients, and specifically to the treatment of atopic dermatitis in mammals by oral treatment.

BACKGROUND

Dermal disorders in companion animals are a common problem. These disorders can be caused by various issues including atopic dermatitis, irritant contact dermatitis, allergic contact dermatitis, yeast infections, folliculitis, impetigo, seborrhea, ringworm, alopecia, mange, flea, tick, dry skin, acral lick dermatitis, hot spots, immune disorders, or skin tumors.

One of the more important dermal disorders is atopic dermatitis. Atopic dermatitis is a form of allergy that is a common problem in 10-15% of all dogs and a similar number in cats. The term atopic in this sense means the animal has a predisposition toward developing certain allergic hypersensitivity reactions associated with an excessive IgE reaction in the skin. Dogs, for example, almost always show allergic reactions through their skin regardless of its source. This means that not only atopy shows as itchy skin, but so do food allergy and insect bite allergy. Some specific signs of canine atopic dermatitis (CAD) include excessive chewing, licking and scratching at the face, paws, abdomen, armpits and genital area. The biting and scratching can cause much hair loss, skin lesions and inflammation.

While allergies can come from food, bacteria, or fleas, atopic dermatitis is typically acquired by inhalation of allergens such as tree pollen, grass pollen, human dander, dust mites, molds, house dust, feathers and other airborne particles. Any airborne particle can potentially become an allergen (irritant) to cause atopic dermatitis. These allergens can result in specific IgE antibodies against them to ultimately cause atopic dermatitis. An atopy/inhalant dog allergy is usually associated with certain areas of the dog's body. This can include areas around the eyes and mouth, the armpits, the abdomen, around the anus, and the legs.

Atopic dermatitis is mediated by the immune system through IgE antibodies, mast cells and histamine release. As a very simplified physiological explanation of atopic dermatitis, allergens, such as pollens, are inhaled or they simply cross the skin where they encounter and bind to IgE molecules present on mast cells of the immune system. The mast cells become activated to release histamine or other mediators. These chemical mediators propagate an excessive inflammatory response characterized by blood vessel dilation, production of pro-inflammatory molecules, cytokine release, and recruitment of leukocytes. This causes redness and swelling of the skin to occur and the subsequent itching response by the dog.

During this sequence of events in atopic dermatitis, arachidonic acid in cell membranes is metabolized to produce the previously mentioned pro-inflammatory molecules that include certain prostaglandins and leukotrienes. The metabolic pathways to produce prostaglandins and leukotrienes are mediated by certain enzymes, including cyclooxygenase I, cyclooxygenase II and 5-lipoxygenase. These enzymes have been favorite targets to inhibit by the drug approach in attempts to alleviate the symptoms of atopic dermatitis. Atopic dermatitis appears to involve multiple 5-Lipoxygenase pathway eicosanoids and receptor subtypes, suggesting that inhibition of the pathway at the level of 5-Lipoxygenase may be necessary for maximal efficacy to reduce atopic dermatitis (Rubin).

While maintaining normal skin health in dogs with CAD has been the goal, CAD is hard to treat under most circumstances as many different factors could be contributing to the problem. Unfortunately, no cure has been found to resolve atopy, but several treatment options are available to control the symptoms. The best solution theoretically is to avoid the allergen. But this may prove to be too difficult a task. A veterinarian might try a sequence of treatment options with the dog, starting with efficient flea control and making sure there are no complicating diseases are occurring in the animal. Then, a trial of various antihistamine drugs in conjunction with the use of fatty acids might take place. If that does not work for the dog, then trials with corticosteroid drugs might occur. If that does not work then hyposensitizing vaccines can be tried to reduce the symptoms of CAD.

There are pros and cons to these traditional drug approaches. There are no guarantees of success with the usual drug orientated treatments. In addition, the usual treatments are costly and can take many months to work. Further, steroid drugs can have undesirable side effects. With antihistamines, it may have to be tried with several different types. Dog allergy vaccinations shots may take a long time to take effect. Additional antibiotics for ear infections or other secondary infections may also have to be used.

An alternative method is needed to help reduce atopic dermatitis that is not drug oriented and does not have the issues associated with the traditional approaches. While no one single approach seems to be fully effective, a combination of elements is required in an alternative approach. However, it is not obvious what the best combination of elements is required or what the best delivery system is for these elements.

Currently, numerous fatty acid supplements are marketed to veterinarians as safe, effective alternatives to systemic glucocorticoids in the treatment of canine pruritic skin disease. The majority of these supplements contain a mixture of polyunsaturated fatty acids (PUFA) including omega-3 PUFA, such as eicosapentaenoic acid (EPA) and docosahexanenoic acid (DHA). In theory, the addition of EPA and DHA to the diet causes the displacement of arachidonic acid (AA) with EPA or DHA in cell membranes and a subsequent decrease in production of pro-inflammatory eicosanoids from AA for the less inflammatory eicosanoids of EPA. This leads to a modification of both platelet and neutrophil responses which in turn decreases clinical evidence of inflammation. Less inflammation means less atopic dermatitis.

Omega-6 fatty acids have also been used in treating atopic dermatitis. The stratum corneum of atopic dogs was characterized by a significant decrease in the lipid content when compared to the healthy controls. Following oral supplementation with a mixture of essential omega-6 and omega-3 fatty acids, the overall lipid content of the stratum corneum markedly increased (Popa). Evening primrose containing omega-6 fatty acid has been shown to help CAD and can be added to the formulation (Scarf).

A dose of 40-50 mg of EPA/kg/day (equivalent to 1 ml of cold water marine fish oil per 4 kg of body weight) has been shown in multiple studies to be somewhat effective in reducing pruritus in CAD (Loga, Mueller). However, only about 15-20% of atopic dogs can be controlled with fatty acid therapy alone while a significant proportion of others have a reduction in pruritus that permits reduction of cortisone doses. However, it can help. Even dogs not obviously responding to fatty acid supplement alone can be treated with lower doses of prednisolone. Withdrawal of polyunsaturated fatty acid therapy and substitution with a control diet in dogs responding to omega-3-omega-6 therapy results in deterioration. As such, supplementing with EPA/DHA and fish oil is a good start, but it is only partially the answer.

The lipid matrix in the stratum corneum is important to the barrier function of mammalian skin. Ceramides are main components of intercellular lipids in the stratum corneum and play an essential role in skin barrier function. Studies suggest that decreased amounts of ceramides in the skin of dogs with CAD may be involved in the impaired barrier function of their skin (Reiter). Ceramide deficiency leads to increased permeability and increased allergen penetration and sensitization. It is currently unknown whether this dysfunction is primary and genetically inherited or secondary to inflammation. However, it is accepted that skin barrier deficiency plays an important role in either starting or minimally exacerbating CAD.

Thus, the therapeutic approach is changing from focusing on the control of the inflammation to a combined approach that includes therapies aimed at skin barrier repair. A study of 4 weeks of topical administration of an emulsion containing ceramides, free fatty acids, and cholesterol (skin lipid complex) led to significantly increased values for ceramides (Ji Young). In another study (Marsella), a commercial topical application of a ceramide-based treatment (ALLERDERM SPOT ON, Virbac, Inc., Fort Worth, Tex.) helped to decrease clinical signs of CAD in dogs that had failed to respond to other therapies. The beneficial effect was most evident after several weeks of therapy with a statistically significant reduction of CADESI and specific reduction of erythema from the baseline after 6 weeks. CADESI is a Canine Atopic Dermatitis Extent and Severity Index, which is a means of objectively assessing the severity of clinical signs in CAD. The authors concluded that this topical treatment modality is best used as adjunctive therapy. Another unpublished study evaluating the same formulation in a blinded and controlled fashion confirmed the beneficial effect in CAD.

All of these studies with ceramides involved the use of topical applications. Topical applications are inconvenient to use and are messy. It has not been obvious to use oral ceramides to treat animals for atopic dermatitis since only small amounts of ceramides have been used in topicals. Further, it is not expected that the amount of oral ceramides used in topical applications could make their way all the way through the gastrointestinal tract and eventually make their way to the skin. Absorbing ceramides from the outer surface of the skin has always appeared to be a far more direct route.

However, some studies have unexpectedly demonstrated that some ceramide orally administered can gradually distribute in the dermis after gastrointestinal absorption, followed by transfer from the dermis to the epidermis (Osomu). Based on these results, it was concluded that the administered ceramide or its metabolite(s) are likely to be involved in the improvement effect on barrier function after arriving in the skin. Other studies have shown that oral intake of glucosylceramide reduced transepidermal water loss in mice and human subjects. (Uchiyama).

Studies have shown that the sphingoids c18:2 and t18:1 activated genes related to de novo ceramide synthesis and increased ceramide production, whereas glucosylceramide and 4-sphingenine could not. These results suggest that the effect of dietary glucosylceramides on the skin is mediated by c18:2 and t18:1 (Shirakura). Nine species of sphingoids are commonly found in plants and many sources of glucosylceramide other than konjac tuber exist, e.g., rice bran, corn, apple, and sugar beet pulp. These glucosylceramides also contain c18:2 and t18:1, but these sphingoids are not as abundant as in konjac, suggesting that konjac is the most effective source of material for improving skin ceramide production. Because the amount of glucosylceramide ingestion is so limited, it is believed that improvement of the skin is not due to the direct localization of glucosylceramide to the skin. At least part of the mechanism involves a triggering of the ceramide synthesis pathway by c18:2 and t18:1. One disclosure, US Patent Publication 2005/0196461 to Udell, is directed to an orally administered formulation containing ceramides in an ingestible soft gelatin capsule for treating conditions such as dry skin and wrinkles in humans. However, such a product has defects in that gelatin capsules are difficult to administer to animals. Further, the composition only appears to attempt to serve as a protective skin barrier, a temporary treatment. It will not prevent further loss of necessary products to alleviate skin conditions.

Thus while there are some products on the market that utilize ceramides in topical and oral applications for dermal use, improvements can be made on the concept. A food composition for animals that (1) contains active ingredients, (2) improves the symptoms of atopic dermatitis for animal, (3) assists in future care of animal skin and (4) can be given as a treat is desirable.

SUMMARY OF THE INVENTION

It is therefore an object of the invention to provide a simple method of orally administrating active ingredients to animals that allow on-going treatment of atopic dermatitis. The active ingredients for treating atopic dermatitis in the invention are not palatable by themselves.

It is a further object of the invention to add beneficial active ingredients in a highly palatable delivery system as mammals with atopic dermatitis will likely receive doses on a daily basis for the rest of their life.

The invention is generally directed to an oral ingestible composition for treating atopic dermatitis in a mammal comprising a therapeutically effective amount of ceramide to treat atopic dermatitis, wherein the composition is present in a soft dough delivery system.

The invention is further directed to an oral ingestible composition for treating atopic dermatitis in a mammal comprising a therapeutically effective amount of ceramide to treat atopic dermatitis; a therapeutically effective amount of a compound to treat atopic dermatitis wherein the compound is selected from the group consisting of at least one of a lipoxygenase inhibitor, an antihistamine, and an immunomodulator; vitamins in therapeutically effective amounts; minerals in therapeutically effective amounts; and omega-3 and omega-6 polyunsaturated fatty acids in therapeutically amounts, wherein the composition is present in soft dough delivery system comprising a carrier base including components selected from the group consisting of powders of flour, an emulsifier, a starch, an oil, a softening agent, and water in a combination and in amounts effective to confer soft dough viscoelasticity to the delivery system.

Further, the invention is directed to an oral ingestible composition for treating atopic dermatitis in a mammal comprising a therapeutically effective amount of a glycosylceramide to treat atopic dermatitis, wherein the glycosylceramide is selected from the group consisting of Konjac tuber, rice, corn, apple, and sugar beet and wheat, wherein the glycosylceramide is present in an amount of from about 0.01% to about 1.0% w/w of the composition; a therapeutically effective amount of a lipoxygenase inhibitor, wherein the lipoxygenase inhibitor is selected from the group consisting of ginger root extract (*Zingibar officinale*) and black cumin (*Nigella sativa*); a therapeutically effective amount of an antihistamine, wherein the antihistamine is licorice (*Glycyrrhiza glabra*) extract; a therapeutically effective amount of an immunomodulator, wherein the immunomodulator is selected from the group consisting of triptolide, garlic, turmeric, and tea present in an amount of from about 0.001% to about 1% w/w of the composition; vitamins in therapeutically effective amounts, wherein the vitamins are selected from the group consisting of vitamin A, vitamin C, vitamin D, vitamin E, vitamin K, vitamin B1, vitamin B2, vitamin B3, vitamin B5, vitamin B6, vitamin B7, vitamin B9 and vitamin B12; minerals in therapeutically effective amounts, wherein the minerals are selected from the group consisting of zinc, manganese, copper and molybdenum; and omega-3 and omega-6 polyunsaturated fatty acids in therapeutically amounts, wherein the omega-3 and omega-6 polyunsaturated fatty acids are selected from the group consisting of plant oils, fish oils, animal oils, algae sources and crustacean sources, EPA and DHA, and evening primrose oil; wherein the composition is present in a soft dough delivery system comprising a carrier base including components comprising: powders of flour, wherein the powders of flour are selected from soy, wheat, oat, barley, brown rice, dried whey powder, liver powder, carrot powder, cherry powder, pineapple powder, alfalfa herb powder in amounts from 0-50% w/w of the composition, an emulsifier, wherein the emulsifier is lecithin present in amounts ranging from about 0 to 20% w/w of the composition, a starch, wherein the starch is selected from potato or corn in amounts ranging from about 0 to 20% w/w of the composition, an oil, a softening agent, and water in a combination and in amounts effective to confer soft dough viscoelasticity to the delivery system.

Further still, the invention is directed to a method of treating atopic dermatitis in a mammal comprising administering an oral ingestible composition, comprising a therapeutically effective amount of ceramide to treat atopic dermatitis; a therapeutically effective amount of a lipoxygenase inhibitor; a therapeutically effective amount of an antihistamine; a therapeutically effective amount of an immunomodulator; vitamins in therapeutically effective amounts; minerals in therapeutically effective amounts; and omega-3 and omega-6 polyunsaturated fatty acids in therapeutically amounts; wherein the composition is present in soft dough delivery system comprising a carrier base including components selected from the group consisting of powders of flour, an emulsifier, a starch, an oil, a softening agent, and water in a combination and in amounts effective to confer soft dough viscoelasticity to the delivery system.

The focus of the present invention is the issue of immunocompromised skin due to impaired skin barrier which is a primary cause of atopic dermatitis. The traditional drug approach to treating atopic dermatitis usually limits itself to a single set of metabolic pathways. Further, the drug approach does not address the barrier function of the skin.

As atopic dermatitis is clearly a very complicated process, involving many different metabolic pathways, the present invention is a novel composition that addresses the multiple metabolic pathways involved while also addressing the barrier aspect of the skin, but in palatable oral delivery system instead of a topical application.

The use of ceramides in oral applications for atopic dermatitis is not obvious to use since only topical applications have been commercialized. Furthermore, the amount of oral ceramides ingested is very limited, so it has been believed that any improvements seen are not due to the direct localization of ceramide to the skin (Shirakura). Although topical application of ceramide is effective in the treatment of atopic dermatitis, its effect is transient (Kimata). These topical strategies are most helpful as adjunctive treatments and would be best used in young patients that have not developed chronic skin changes. Importantly, treatment for atopic dermatitis is multimodal and tailored to the individual patient, the age, and the duration of the disease.

While not necessary to achieving the superior effects of this invention, the addition of ingredients such as triptolide, ginger and *Nigella sativa* makes the ceramide more effective and will prevent the further loss of exogenously administered ceramide, because the above three ingredients are working on the pathology of the disease.

The issue of skin barrier repair has partially been addressed both with oral administration of essential fatty acids and the topical application of products containing a combination of ceramides and fatty acids. While oral ceramides by themselves have efficacy, the efficacy also can be improved by adding other active ingredients that are intended to reduce atopic dermatitis. However, the oral format chosen also is critical to success in animals. The present invention is intended to combine the efficacy of oral ceramides into a critical soft chew format. In addition, the ingredient combination of the present invention in a soft chew oral delivery system is also an innovative combination of ceramides and other components in a conveniently deliverable form.

While drugs have their place, an approach to atopic dermatitis is desired that does not involve drugs but yet does address the multiple metabolic pathways and skin barrier issues that are involved in atopic dermatitis. The present invention takes into account the underlying causes and the symptoms of atopic dermatitis. To accomplish this innovative approach, the active ingredients should have antihistamine action. 5-Lipoxygenase produces inhibitory action, while helping with skin barrier functions and overall coat health, and while being cost effective. This can be accomplished through the use of certain phytobotanic extracts and certain fatty acids such as EPA and DHA.

The use of ceramides alone or in combination of other active ingredients in a soft dough delivery system is an innovative approach to treating atopic dermatitis. Atopic dermatitis is a chronic problem and needs long term treatment. Therefore, a palatable format is necessary for administration and easier on the pet and pet owner. Gelatin capsules/tablets/lozenges are hard to give to an animal because the pet owner has to force it into the animal's mouth. This is generally not an acceptable practice to the pet owner over the long term of six (6) months on a daily basis.

The critical advantages of a soft chew format over a gelatin capsules, lozenge or tablets are that soft chews are highly palatable to animals whereas capsules, tablets or liquids are not nearly as palatable or easy to administer. Lozenges, i.e. slow dissolving compositions, are not are not an effective or practical format for animals since dogs, for example, simply will gulp the lozenge down rather than allow it to stay in the mouth as required. It is not obvious, but better palatability means better compliance. The soft chew oral delivery system provides better compliance than other oral formats. While not obvious, the uninterrupted treatment from better compliance keeps the ceramide levels up in the animal's system, leading to better treatment outcome when using a soft chew formulation. While not obvious, the soft chew format easily breaks down in the stomach, dissolves faster and is better absorbed in the system. Capsules take longer to dissolve in the system of a dog and take longer to be absorbed and therefore will take longer to see efficacy. Thus, the soft chew delivery system of the present invention is critical to providing the benefit of enhancing stability and palatability of the product.

The objects and advantages of the invention will appear more fully from the following detailed description of the preferred embodiment of the invention.

DETAILED DESCRIPTION OF THE INVENTION

The present invention employs the use of a soft food delivery system for the oral administration of ceramide in concert with another ingredient, which together forms a synergistic beneficial therapeutic effect on the animal.

Ceramides

Ceramides are a complex family of waxy lipid molecules. A ceramide is composed of sphingosine and a fatty acid. Sphingosine (2-amino-4-octadecene-1,3-diol) is an 18-carbon amino alcohol with an unsaturated hydrocarbon chain. A fatty acid is a carboxylic acid with a long aliphatic tail (chain), which is either saturated or unsaturated. Ceramides are found in high concentrations within the cell membrane of cells. They are one of the component lipids that make up sphingomyelin, one of the major lipids in the lipid bilayer. Ceramides and other sphingolipids found in the cell membrane play a structural role in cells, but can also participate in a variety of cellular signaling include regulating differentiation and proliferation of cells. Adding sugar molecules to the ceramide compound creates a group of molecules called glycosylceramides. When the sugar is glucose, the molecule is called a glucosylceramide. Glucosylceramide is a major constituent of skin lipids, where it is essential for lamellar body formation in the stratum corneum and to maintain the water permeability barrier of the skin. In addition, the epidermal glucosylceramides (together with sphingomyelin) are the source of the unusual complex ceramides that are found in the stratum corneum, including those with estolide-linked fatty acids.

Oral ceramides from Konjac root have been used in Japan and appear to be safe. In 2004, New Dietary Ingredient ("NDI") Notification was submitted pursuant to 21 C.F.R. 0 190.6 and Section 8 of the Dietary Supplement Health and Education Act. This Notification concerned the new dietary ingredient phyto-derived Ceramides, a type of lipids which are constituents of sphingolipids, and for this Notification, derived from either wheat or rice. Oral application of glycosylceramide has been used in one published case study of on a dog (Manoru). The results concluded that oral supplementation can improve CAD.

Providing building blocks of ceramides and omega fatty acids to help the barrier function of the skin is important, but blocking the underlying causes of atopic dermatitis in animals is also required. Use of certain botanical extracts is a safe way of treating animals to block underlying causes of atopic dermatitis. However, the specific botanical extracts used are the challenge. Examples of suitable glycosylceramides sources include konjac tuber, rice, corn, apple, sugar beet and wheat. The term ceramide includes all ceramides, whether naturally or synthetically derived, i.e., animal or vegetable.

The oral ceramide may be included in an amount of from about 0.01% to about 1.0% w/w of the viscoelastic mass, preferably from about 0.02% to about 0.10% w/w, and more preferably from about 0.04% to about 0.08% w/w.

Lipoxygenase Inhibitor

Black Cumin (*Nigella sativa*) has been shown to be effective in helping treat a number of immune-related disorders including psoriasis (*Sharrif*). While it has numerous compounds, nigellone, one of its major actives, has been shown to inhibit the release of histamine from mast cells (Chakravarty). It also inhibits 5-lipoxygenase product formation and has anti-inflammatory activity (El-Dakhakhny). Black cumin also is an Association of American Feed Control Officials (AFFCO) approved ingredient. Black Cumin can be provided in the form of an extract such as an oil, a powder, or other forms.

Ginger root extract (*Zingibar officinale*) has been used as a calming agent in nutraceutical supplements, but the anti-inflammatory properties of ginger have been known and valued for centuries. Ginger has lipoxygenase inhibition action (Grzanna) and has antihistamine activity (Supinya). Formulas containing ginger have been efficacious and safe to treat recalcitrant atopic dermatitis (Kobayashi). Ginger is an AAFCO approved ingredient.

Other lipoxygenase inhibitors from herbal sources include catechins such as epicatechin, epigallocatechin gallate, epigallocatechin and others from tea (*Camellia sinensis*) allicin from garlic (*Allium sativum*); caffeic acid from dandelion (*Taraxacum officinale*) (Subhuiti). These herbals are safe and are AFFCO approved ingredients. The amount of the herbal extract included in the viscoelastic mass can be adapted to the specific needs of the target animal.

The lipoxygenase inhibitors may be included in an amount of from about 0.001% to about 10.0% w/w of the viscoelastic mass, preferably from about 0.01% to about 5% w/w, and more preferably from about 1.0% to about 3.5% w/w.

Antihistamine

Licorice (*Glycyrrhiza glabra*) is a traditional botanical that has been used as an anti-allergy agent, anti-inflammatory agent, and anti-asthmatic agent. Research shows that licorice works through IgE production inhibitory actions and through antihistamine activity (Saeedi). Licorice has been effective for treating atopic dermatitis and also is an approved AFFCO approved ingredient (Yong-Wook). Licorice components given orally have been shown to reduce allergan-induced scratching behavior in animals (Saeedi).

Extracts of basil, ginger, thyme, origanum and caraway are also known to have antihistamine capability. These are all natural compounds and are AFFCO approved. The amount of the licorice or other listed herbal extract included in the viscoelastic mass can be adapted to the specific needs of the target animal. As an example, licorice extract may be included in an amount of from about 0.001% to about 7.0% w/w of the viscoelastic mass, preferably from about 0.01% to about 5.0% w/w, and more preferably about 1.0% to about 2.0% w/w.

Immunomodulator

Treatment of atopic dermatitis is commonly done with drugs, like cyclosporine, that decrease the activity of the immune system. There can be undesirable side effects when using drugs like cyclosporine. The use of botanical extracts that would decrease the activity of the immune system without side effects is therefore desirable for atopic dermatitis. Extracts from *Tripterygium wilfordii* containing triptolide, has a long history of use in traditional Chinese medicine to treat immune-related disorders. These extracts have been used to treat inflammation including atopic dermatitis. Triptolide appears to have a suppressive effect on the immune system, and it inhibits the development and spread of inflammation.

Triptolide inhibits the transcription of the p40 gene encoding the shared subunit of IL-12 and IL-23 in APCs (Yan). The immunosuppressive effect of triptolide on T cells has been somewhat characterized. It inhibits T cell activation and cytokine gene transcription in T cells and suppresses the expression of genes for transcription factors, signal transduction pathway regulators, DNA binding protein, and MAPK in Jurkat cell. In addition, triptolide inhibits lymphocyte activation and T cell expression of IL-2 at the level of transcription by inhibiting NF-κB transcriptional activation.

However, little is known about the effect of triptolide on accessory cells, particularly the professional APCs, such as dendritic cells (DCs) and macrophages. It has been suggested that DCs are a primary target of the immunosuppressive activity of triptolide. At high concentrations (≥20 ng/ml) triptolide induces apoptosis of DCs through sequential p38 MAP kinase phosphorylation and caspase 3-activation. It has also been shown that triptolide inhibits DC-mediated chemoattraction of neutrophils and T cells through inhibiting Stat3 phosphorylation and NF-κB activation. Triptolide prevents the differentiation of immature monocyte-derived DC (MoDC) by inhibiting CD1a, CD40, CD80, CD86, and HLA-DR expression, and by reducing the capacity of MoDC to stimulate lymphocyte proliferation in allogeneic MLR. However, expression of surface CD14 and phagocytic capacity of MoDC was enhanced by triptolide. Therefore, the suppression of DC differentiation, maturation, and function of immature DCs by triptolide may explain some of its immunosuppressive properties.

The amount of triptolide included in the viscoelastic mass can be adapted to the specific needs of the target animal. As an example, triptolide may be included in an amount of from about 0.001% to about 1% w/w of the viscoelastic mass, preferably from about 0.005% to about 0.05% w/w, and more preferably from about 0.01% to about 0.03% w/w.

Other immunomodulators that are from natural herbal sources include garlic, turmeric, and tea. These are AFFCO-approved ingredients. Vitamins A, C, and E are also known to be immunomodulators. These are also all AFFCO approved ingredients.

Polyunsaturated Fatty Acids

Omega-3 and omega-6 fatty acids (also called ω-3 and ω-6 fatty acids or n-3 and n-6 fatty acids) are polyunsaturated fatty acids (PUFAs) with a double bond (C=C) at the third or sixth carbon atom from the end of the carbon chain for the omega 3 and omega 6, respectively. The fatty acids have two ends, the carboxylic acid (—COOH) end, which is considered the beginning of the chain, thus "alpha", and the methyl (CH3) end, which is considered the "tail" of the chain, thus "omega." The way in which a fatty acid is named is determined by the location of the first double bond, counted from the methyl end, that is, the omega (ω-) or the n-end.

The three types of omega-3 fatty acids involved in mammalian physiology are α-linolenic acid (ALA), found in plant oils, eicosapentaenoic acid (EPA), and docosahexaenoic acid (DHA), both commonly found in marine oils. Marine algae and phytoplankton are primary sources of omega-3 fatty acids. Common sources of plant oils containing the omega 3 ALA fatty acid include walnut, edible seeds, clary sage seed oil, algal oil, flaxseed oil, Sacha Inchi oil, Echium oil, and hemp oil, while sources of animal omega-3 EPA and DHA fatty acids include fish oils, egg oil, squid oils, and krill oil. Omega 3 and omega 6 fatty acids are selected from the group consisting of plant oils, fish oils, animal oils, algea sources and crustacean sources. Evening primrose oil is an excellent source of omega 6 polyunsaturated fatty acids. Linoleic acid (18:2, n-6), the shortest-chained omega-6 fatty acid, is one of many essential fatty acids and is categorized as an essential fatty acid because mammals cannot synthesize it. Mammalian cells lack the enzyme omega-3 desaturase and therefore cannot convert omega-6 fatty acids to omega-3 fatty acids.

The amount of omega 3 and omega 6 polyunsaturated fatty acids included in the viscoelastic mass can be adapted to the specific needs of the target animal. As an example, omega 3 and omega 6 polyunsaturated fatty acids may be included in an amount of from about 0.001% to about 25% w/w of the viscoelastic mass, preferably from about 1.0% to about 20.0% w/w, and more preferably from about 8.0% to about 15.0% w/w.

There are also a number of minerals and vitamins that help maintain the immune system. These include zinc, vitamin A, vitamin B12, vitamin E, vitamin C. These vitamins and minerals act as cofactors in enzymatic reactions that are required by the immune system to help maintain normal skin health (Kumary). These vitamins and minerals are a key aspect in formulations that address skin health of dogs.

Vitamins

The composition may include one or more vitamins. Vitamins are necessary for literally tens of thousands of different chemical reactions in the body. They often work in conjunction with minerals and enzymes to assure normal digestion, reproduction, muscle and bone growth and function, healthy skin and hair, clotting of blood, and the use of fats, proteins, and carbohydrates by the body. For example, vitamin E isomers (mixed tocopherols) are antioxidants that help protect animals from free radical damage. Vitamin deficiencies can occur in an animal if poor quality food is provided to the animal. Vitamin deficiencies can also occur if an animal is under stress. Ill or recovering animals that may have a poor appetite typically need a vitamin supplement since they are not receiving their daily requirements through the food they eat. Animals in other situations such as stress from travel, showing, training, hunting, breeding, or lactation can also benefit from vitamin supplementation. Older animals can also benefit from vitamin supplementation. Older animals tend to absorb fewer vitamins, minerals, and electrolytes through the intestinal tract, and lose more of them through the kidneys and urinary tract. Also, some older animals eat less (due to conditions such as oral disease) and may not receive their daily needs of vitamins and minerals. These same old animals are often the ones that will also be given solid medications to treat other conditions. Another issue that may increase the need for vitamin supplementation in animals is that commercial feeds typically involve a heating process that can destroy vitamins present in the feed. The viscoelastic mass of the delivery system described below does not involve heat for manufacture and is therefore able to provide vitamins that are not degraded.

Any vitamin known in the art may be included in the composition of the present invention. Particular vitamins may be provided according to the nutritional requirements of the target animal. Suitable vitamins include both water soluble and/or fat soluble vitamins. Exemplary water soluble vitamins include any or all of the B vitamins (Vitamin $B_1$, $B_2$, $B_3$, $B_4$, $B_5$, $B_6$, $B_7$, $B_8$, $B_9$, $B_{10}$, $B_{11}$, and $B_{12}$) and/or Vitamin C (ascorbic acid). Exemplary fat soluble vitamins include Vitamin A, Vitamin D, Vitamin E, and Vitamin K. As stated above, vitamins A, C, and E also function as immunomodulators. The fat-soluble vitamins may be provided as an element of oils utilized in the present invention, such as, for example, canola oil, corn oil, soybean oil, and vegetable oil. The amount of the vitamins included in the viscoelastic mass can be adapted to the specific needs of the target animal. As an example, each vitamin may be included in an amount of from about 0.001% to about 10.0% w/w of the viscoelastic mass, preferably from about 0.01% to about 5.0% w/w, and more preferably from about 0.5% to about 1% w/w.

Minerals

Minerals play important roles in many biochemical functions in the body. Deficiencies of minerals can lead to problems in the immune system. However supplementation of zinc and copper can help correct these problems. As absorption of chelated minerals to amino acids or other substances is enhanced, this invention uses chelated minerals. This invention uses chelated copper, zinc, manganese and molybdenum to benefit the immune system. The preferred concentration of copper is from 0.1 mg to 2 mg/kilogram; for zinc is from 100 mg to 300 mg/kilogram; and for manganese is from 0.05 mg to 0.2 mg/kilogram.

A typical formulation for a dog is:

| Ingredient | Quantity/Concentration |
|---|---|
| Ceramide | 0.0625% w/w |
| Nigella sativa | 0.63% w/w |
| Zingibar officinale | 0.63% w/w |
| Licorice | 6.3% w/w |
| Triptolide | 0.025% w/w |
| Omega-3 PUFA | 12.5% w/w |
| Vitamin A | 150 IU/g |
| Vitamin B12 | 0.00010% w/w |
| Vitamin C | 0.005% w/w |
| Vitamin E | 2.5 IU/g |
| Copper | 0.0625% w/w |
| Manganese | 0.0275% w/w |

A typical formulation for a cat is:

| Ingredient | Quantity/Concentration |
|---|---|
| Ceramide | 0.02% w/w |
| Nigella sativa | 0.20% w/w |
| Zingibar officinale | 0.20% w/w |
| Licorice | 2.3% w/w |
| Triptolide | 0.008% w/w |
| Omega-3 PUFA | 4.1% w/w |
| Vitamin A | 50 IU/g |
| Vitamin B12 | 0.00003% w/w |
| Vitamin C | 0.0016% w/w |
| Vitamin E | 0.8 IU/g |
| Copper | 0.002% w/w |
| Manganese | 0.009% w/w |

Delivery System

The base composition of the delivery system is comprised of a base powder, lecithin, glycerol, molasses, sugar, starch, mixed tocopherols, sodium chloride, preservatives and water mixed together to form a soft dough composition and extruded. The composition of the present invention comprises a viscoelastic mass. The viscoelastic mass is an edible, dough-like composition that is capable of being folded, wrapped, or rolled around a medicine or otherwise manipulated to surround the medicine to conceal or mask the flavor of the medicine. The viscoelastic mass comprises a carrier base and one or more effector components.

Base Powder: The base powder generally provides structural integrity to the mass. The base powder may comprise a plant powder, an animal powder, or both a plant and an animal powder. Plant powders are powders derived from plants, such as flours or other powders. The flours may be whole flours or flours which have had fractions, such as the germ fraction or the husk fraction, removed. Non-limiting examples of suitable plant powders include soy flour, wheat flour, whole wheat flour, whole wheat fine flour, wheat feed flour, wheat gluten, pre-gel wheat flour, soy protein concentrate, oat flour or powder, barley powder or flour, brown rice flour or powder, dried whey powder, carrot powder, cherry powder, pineapple powder, and alfalfa herb powder. Animal powders are powders derived from animals and can include dehydrated meat byproducts, such as liver powder. In a preferred version of the invention, the base powder comprises an animal powder and a plant flour, which can be mixed with a fluid lubricant. The powder is preferably included in an amount of from about 0% to about 50% w/w of the viscoelastic mass.

Starch: The delivery system may include a starch. As used herein, "starch" refers to any substance comprised of more than about 80%, 90%, 95%, or even 99% amylase and amylopectin by weight. Starches from various sources are known in the art. Suitable starches can be obtained from tuberous foodstuffs, such as potatoes, tapioca, and the like. Other suitable starches can be obtained upon grinding cereal grains such as corn, oats, wheat, milo, barley, rice, and others. The starch may be included in an amount of from about 0% to about 2% w/w of the composition, such as from about 1% to about 15% w/w or from about 5% to about 9% w/w.

Emulsifiers: The composition may include an emulsifier. Suitable emulsifiers include nonionic surfactants, such as polyoxyethylated castor oil, polyoxyethylated sorbitan monooleate, sorbitan monostearate, ethyl alcohol, glycerol monostearate, polyoxyethylene stearate, and alkylphenol polyglycol ethers; ampholytic surfactants, such as disodium N-lauryl-B-iminodipropionate and lecithin; and anionic surfactants, such as sodium lauryl sulphate, fatty alcohol ether sulphates, and mono/dialkyl polyglycol ether orthophosphoric ester monoethanolamine salt. A preferred emulsifier is lecithin, such as soy lecithin. The emulsifier may be included in an amount of from about 0% to about 20% w/w of the composition, such as from about 4% to about 16% w/w or from about 6% to about 10% w/w.

Softening Agents: In order to provide an edible soft chew, the composition preferably includes a softening agent. Examples of suitable softening agents include glycerol and propylene glycol, wetting agents such as cetyl alcohol and glycerol monostearate, and other humectants. Glycerin is a preferred softening agent and can maintain the softness of the composition over the shelf life of the product. The softening agent may be included in an amount of from about 0% to about 50% w/w of the composition, such as from about 5% to about 25% w/w or from about 9% to about 14% w/w.

Flavorings: A flavoring is preferably included in the composition to enhance the palatability of the mass and to mask the flavor of any medicine included therewith. The flavoring is preferably food grade quality. Sweeteners constitute one type of suitable flavoring. Examples of suitable sweeteners include such sugars as xylose, ribose, sucrose, mannose, galactose, fructose, dextrose, and maltose. Other suitable sweeteners include molasses, honey, maple syrup, and fruit flavoring. The sweeteners may be in powdered, granulated, or liquid form. Natural or synthetic sweeteners are suitable. Preferred sweeteners include powdered sugar and dry molasses. Other suitable flavorings include carob, peanuts, garlic, and herbs such as, parsley, celery, peppermint, and spearmint. Natural and synthetic flavoring oils can also be included as a flavoring. Examples of flavoring oils include anise oil, spearmint oil, peppermint oil, cinnamon oil, wintergreen oil, citrus oils, such as lemon, orange, grape, lime, and grapefruit oils. Other suitable flavorings include fruit essences such as apple, strawberry, cherry, and pineapple essences, among others. The flavoring may be included in an amount of from about 0% to about 20% w/w of the viscoelastic mass, such as from about 2% to about 15% w/w, or from about 5% to about 10% w/w.

Antioxidants: The composition preferably includes an antioxidant. Examples of suitable antioxidants include alpha-tocopherol, alpha-tocopherol acetate, butylated hydroxytoluene (BHT), ascorbic acid, mixed tocopherols, propyl gallate, and mixtures thereof. The antioxidant may be included in an amount of from about 0% to about 0.3% w/w of the composition, such as from about 0.025% to about 0.2% w/w, or from about 0.05% to 0.15% w/w.

Preservatives: The composition preferably includes a preservative to prevent or retard growth of microorganisms and fungi. Suitable preservatives include potassium sorbate, methylparaben, propylparaben, sodium benzoate, calcium propionate, or combinations thereof. A preferred preservative comprises a combination of potassium sorbate, methylparaben, and propylparaben. The preservatives may be included in an amount of from about 0% to about 1% w/w of the viscoelastic mass, such as from about 0.03% to about 0.75% w/w or from about 0.05% to about 0.75% w/w.

Salts: The composition preferably includes one or more salts comprising mono- and/or divalent cations for proper gelation of the mass. Suitable sources of mono- and divalent cations include sodium, potassium or calcium salts such as sodium chloride, potassium chloride, calcium chloride, or potassium citrate, among others. Such a salt may be included in an amount of from about 0% to about 5% w/w of the viscoelastic mass, such as from about 0.1% to about 2.5% w/w or from about 0.4% to about 0.6% w/w.

Water and Oil: The composition preferably includes water in an amount of from about 1% to about 50% w/w of the viscoelastic mass, such as from about 1% to about 30% w/w or about 5% to about 15% w/w. The composition preferably includes an oil in an amount of from about 1% to about 50% w/w of the composition, such as from about 1% to about 30% w/w or about 5% to about 15% w/w. Suitable oils include, for example, canola oil, corn oil, soybean oil, and vegetable oil, among others.

Amounts of Components: The amounts of each of the components in the composition may be varied from the amounts described herein depending upon the nature of the delivery drug, the weight and condition of the animal to be treated, and the unit dosage desired. Those of ordinary skill in the art will be able to adjust dosage amounts as required.

Preparation: The individual ingredients in the composition of the invention are mixed together in a standard mixing apparatus. The dry powders are mixed initially. This is followed by the addition of liquid materials to create a soft dough that is easily pliable by hand. The materials are mixed until the dough composition has reached a satisfactory pliability texture level and no dry materials are present. The dough is then transferred to an extruder device hopper. The extruder device hopper feeds the soft dough through an extrusion port, and a knife blade chops the extruded dough composition to a desired length and weight. The cut pieces of the invention are subsequently packaged.

The extruded dough can form any cross-sectional shape depending on the extrusion port design. Suitable shapes include rectangles, squares, circles, triangles, or other specific shapes such as animal or bone shapes. A preferred cross-sectional shape is a thin rectangle. The extruded dough can also have any length, which is determined by the distance between the knife cuts as the dough leaves the extrusion port. The size of the final product may be varied depending on the size of the target animal and the size of the solid medication to be wrapped. In a preferred version of the invention, the viscoelastic mass takes the form of a sheet, i.e., having a depth less than about half the magnitude of the length and width, such as a depth less than about a quarter the magnitude of the length and width.

The extruded dough can be in any shaped designed depending on the extrusion port design. These shape range from a shapeless mass, cylinders, rectangles, squares, circles, triangles, or other specific shapes such as animals or bones shapes.

Use: The composition can take any of several semi-solid of soft dough format in the shape of pills, tablets or boluses. The composition can be administered to any animal, including mammals, in need of nutritional supplementation and/or a particular medication. Non-limiting examples of suitable animals include, dogs, cats, horses, cows, pigs, goats, and sheep, among others. The composition is preferably used with dogs.

Example 1

Ingredients as found in Table 1 were mixed together by first mixing the dry materials in a mixing device followed by mixing in the liquid ingredients to create a base composition. The mixing resulted in a soft dough that was extruded through an extrusion device. The dye shape on the extruder resulted in cylinder shaped pieces that were cut into 8 grams pieces. The extruded shaped material was packaged.

TABLE 1

Base composition of Soft Dough Delivery System

| Ingredient | % w/w |
|---|---|
| Soy Flour | 9.80% |
| Soy Lecithin | 8.00% |
| Pregelatinized Starch | 7.00% |
| Dry Molasses | 14.00% |
| Soy Oil | 7.90% |
| Glycerine | 11.00% |
| Poultry Liver Powder | 12.00% |
| Potassium Sorbate | 0.50% |
| Sodium Chloride USP | 0.50% |
| Powder Sugar | 5.00% |
| Mixed Tocopherols | 0.10% |
| Whole Wheat Fine Flour | 15.50% |
| Water | 8.50% |
| Methylparaben | 0.1 |
| Propylparaben | 0.1 |

Example 2

Palatability trials were conducted on the base composition found in table 1. Twenty dogs were given single 8 gram pieces of the composition. All of the dogs consumed the composition within 10 seconds. This indicated that the base composition of the invention was palatable to the dog.

Example 3

Active ingredients found in Table 2 were mixed into base compositions of Table 1 to create 100 lbs of total mixture. The composition was extruded and cut into 8 gram pieces as described in Example 1. Twenty dogs were given single 8 grams pieces of the base composition with active ingredients. All of the dogs consumed the oral dose within 10 seconds. This indicates that the active ingredients for treating atopic dermatitis were successfully masked by the base composition of the invention.

TABLE 2

Active Ingredients

| | |
|---|---|
| Black Seed Oil | 6.3 lbs |
| Ginger Powder | 0.63 lbs |
| Licorice powder | 6.3 lbs |
| Omega 3 DHA beadlets MEG-3 ® DHA Powder | 12.5 lbs |
| Konjac Ceramides | 0.0625 lbs |
| Zin Pro 180 (zinc) | 0.15 lbs |
| Vitamin A 500,000 IU, | 0.03 lbs |
| Vitamin B-12 (1%) | 0.01 lbs |
| Vitamin E 50% (500 IU) | 0.25 lbs |
| Ascorbic Acid (99-100%) | 0.7 lbs |

Example 4

A clinical trial was set up to examine the efficacy of the invention. Dogs with diagnosed with non-seasonal atopic dermatitis using the William's clinical criteria [Williams, R R, et al] were selected and based on being >1 year of age and >5 lbs weight but otherwise being healthy. Exclusion criteria for the trial included clinical evidence of active ectoparasite infestation, bacterial, fungal skin infection, pyoderma, malassezia dermatitis or mange; concurrent or within 21 days use of immunosuppressant, glucocorticoids, antihistamines, anti-inflammatory (NSAIDs) or antibiotic treatment; if the dogs had been using essential fatty acid supplement within 21 days before the start of the trial; dogs with hypothyroidism, active or uncontrolled flea allergy and food allergy were excluded.

The dose was administered in the form of two soft chew with actives as in example 3 twice daily with or without food for eight weeks. During the trial animals were evaluated at day 0, at two weeks, 4 weeks and at final visit at 8 weeks.

The direct effect of treatment was measured by the CADESI. This index is based on the presence and intensity clinical indicators such as erythema, lichenification, alopecia (hair loss) and excoriation on different skin areas. A of score 0 indicates no visible problems are present while a score of 1 or 2 indicates mild or moderate condition and a score of 5 indicates the most severe conditions.

Results: Prior to treatment, the dog has a skin lesion that is erythematous and inflamed. There was lichenification of skin with alopecia. A CADESI score of 4 was given to this animal before treatment. After 8 weeks of oral treatment, there was a reduction in the amount of erythematous skin tone and a reduction in lesion size. While alopecia has not improved at lesion site at this time point in the trial, that may be due to damage of hair follicles that ultimately can grow back. The reduction in erythema redness that is very evident after the treatment that might be accounted for by a reduction in rubbing or scratching of the skin by the dog, especially as concurrent skin health improves. There was an improvement in the CADESI score to a level of 2 after the treatment with the invention. The improvement in CADESI score in this animal is consistent with the efficacy of the invention.

Example 5

The same trial set up as found in example #4 was carried out in another dog. Prior to treatment, there was a lichenified lesion present with diffuse thickening and hardening of skin, along with alopecia. The alopecia might have been the result of excessive pruritus and scratching. However there is no erythematous lesion in this case. The CADESI value was evaluated to be 5 before treatment. After 8 weeks of treatment with the invention, there was visible growth in hair at lesion site and reduction in scabbed and lichenified skin. The CADESI score was evaluated to be 2. This shows skin health improvement when using the invention. These improvements in CADESI score results are consistent with the efficacy of the invention.

Any version of any component or method step of the invention may be used with any other component or method step of the invention. The elements described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference in their entirety to the same extent as if each individual reference were specifically and individually indicated as being incorporated by reference. In case of conflict between the present disclosure and the incorporated references, the present disclosure controls.

The devices, methods, compounds and compositions of the present invention can comprise, consist of, or consist essentially of the essential elements and limitations described herein, as well as any additional or optional steps, ingredients, components, or limitations described herein or otherwise useful in the art.

While this invention may be embodied in many forms, what is described in detail herein is a specific preferred embodiment of the invention. The present disclosure is an exemplification of the principles of the invention is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting since the scope of the present invention will be limited to only the appended claims and equivalents thereof.

BIBLIOGRAPHY

US Patent Publication 2005/0196461 to Udell, entitled "Ceramide formulations suitable for oral administration."

El-Dakhakhny M., et al., "*Nigella sativa* oil, nigellone and derived thymoquinone inhibit synthesis of 5-lipoxygenase products in polymorphonuclear leukocytes from rats," Journal of Ethnopharmacology, 81, 161-164, 2002.

Grzanna R, et al., "Ginger—an herbal medicinal product with broad anti-inflammatory actions," J Med Food. 8:125-32, 2005.

Ji-young Jung, et al., "Clinical use of a ceramide-based moisturizer for treating dogs with atopic dermatitis," Vet. Sci. (2013), 14(2), 199-205.

Kimata H., "Improvement of atopic dermatitis and reduction of skin allergic responses by oral intake of konjac ceramide," Pediatr Dermatol. 2006 July-August; 23(4):386-9.

Kobayashi H, et al., "Diet and Japanese herbal medicine for recalcitrant atopic dermatitis: efficacy and safety," Drugs Exp Clin Res. 30:197-202, 2004.

Kumary P., et al., "Role of Micro-Nutrients in Dermatological Disorders of Dog," INTAS POLIVET (2007) Vol. 8 No. II: 467-471.

Logas D and Kunkel G A, "Double blinded crossover study with marine oil supplementation containing high dose eicosapentaenoic acid for the treatment of canine pruritic skin disease," Vet. Dermatology 5:99-104, 1994.

Manoru Onuma, et al, "A case study of canine atoptic dermatitis administered with oral glucosylceramide supplementation," Jpn J Vet Dermatorl 2008, 14: 81-83.

Marsella R., et al., "Investigations on the Effects of a Topical Ceramides-Containing Emulsion (Allerderm Spot on) on Clinical Signs and Skin Barrier Function in Dogs with Topic Dermatitis: a Double-Blinded, Randomized, Controlled Study," Intern J Appl Res Vet Med, Vol. 11, No. 2, 2013.

Meuller R. S., et. al. "Effect of omega-3 fatty acids on canine atopic dermatitis," Journal of Small Animal Practice. 45, 293-297, 2004.

Osamu UEDA, et al., "Distribution in Skin of Ceramide after Oral Administration to Rats," Drug Metab. Pharmacokinet. 24 (2): 180-184 (2009).

Paterson S, "Additive benefits of EFAs in dogs with atopic dermatitis after partial response to antihistamine therapy," Journal of Small Animal Practice, 36: 389-394, 1995.

Popa I., et al., "Analysis of epidermal lipids in normal and atopic dogs, before and after administration of an oral omega-6/omega-3 fatty acid feed supplement. A pilot study," Veterinary Research Communications, 2011, 35, 8, pp 501-509.

Reiter L. V., et al., "Characterization and quantification of ceramides in the nonlesional skin of canine patients with atopic dermatitis compared with controls," Vet Dermatol. 2009 August; 20(4):260-6.

Rubin P., et al., "Pharmacotherapy of diseases mediated by 5-lipoxygenase pathway eicosanoids," Prostaglandins Other Lipid Mediat. 83:188-97, 2007.

Rosanna Marsella, "An update on the treatment of canine atopic dermatitis," Veterinary Medicine: Research and Reports 2012:3 85-91.

Saeedi M., et al., "The treatment of atopic dermatitis with licorice gel," Journal of Dermatological Treatment 14, 153-157, 2003.

Scarff D. H.; et al., "Double blind, placebo-controlled, crossover study of evening primrose oil in the treatment of canine atopy," Veterinary Record, 1992, 131, 5, pp 97-99.

Shand Moghaddasi M., "*Nigella Sativa* Traditional Usages (Black Seed)," Advances in Environmental Biology, 5: 5-16, 2011.

Shirakura et al., "4,8-Sphingadienine and 4-hydroxy-8-sphingenine activate ceramide production in the skin," Lipids in Health and Disease 2012, 11:108.

Subhuti Dharmananda, "Reducing Inflammation with diet and supplements: The Story of Eicosanoid Inhibition," Institute for Traditional Medicine, Portland, Oreg. General Review. 2003.

Supinya Tewtrakul and Sanan Subhadhirasakul, "Antiallergic activity of some selected plants in the Zingiberaceae family," Journal of Ethnopharmacology 109: 535-538, 2007.

Tsuji K, et al., "Dietary glucosylceramide improves skin barrier function in hairless mice," J Dermatol Sci 2006 November; 44(2):101-7.

Uchiyama Taro, et al., "Oral intake of glucosylceramide improves potentially higher level of transepidermal water loss in mice and health human subjects," Jr. of Health Science 54: 599, 2008.

Williams R R, et al., "Diagnosing heterozygous familial hypercholesterolemia using new practical criteria validated by molecular genetics," Am J Cardiol. 1993; 72:171-6.

Yong-Wook Shin, et al, "In-vitro and in-vivo anti-allergenic effects of *Glycyrrhiza glabra* and its components," Planta Medica 73: 257, 2007.

Yoshii, H., et al., "Oxidation stability of eicosapentaenoic and docosahexaenoic acid included in cyclodextrins," Journal of inclusion phenomena and molecular recognition in chemistry 1996, Volume 25, Issue 1-3, pp 217-220.

Yan Zhang and Xiaojing Ma, "Triptolide Inhibits IL-12/IL-23 Expression in APCs via CCAAT/Enhancer-Binding Protein a," J Immunol. Apr. 1, 2010; 184(7): 3866-3877.

What is claimed is:

1. An oral ingestible composition for treating atopic dermatitis in a mammal, the composition comprising:

active ingredients mixed throughout a soft dough carrier base,
wherein the active ingredients are present in the composition in an amount therapeutically effective to treat atopic dermatitis, and wherein the active ingredients comprise:
ceramide in an amount of from about 0.01% to about 1.0% w/w of the composition;
a lipoxygenase inhibitor comprising at least one of black cumin (*Nigella sativa*) and ginger root (*Zingibar officinale*) extract;
licorice (*Glycyrrhiza glabra*) extract;
triptolide;
vitamins selected from the group consisting of vitamin A, vitamin C, vitamin D, vitamin E, vitamin K, vitamin B1, vitamin B2, vitamin B3, vitamin B5, vitamin B6, vitamin B7, vitamin B9, and vitamin B12;
minerals selected from the group consisting of zinc, manganese, copper, and molybdenum; and
polyunsaturated fatty acids selected from the group consisting of omega-3 fatty acids and omega-6 fatty acids in an amount of from about 8.0% to about 15% w/w of the composition; and wherein the soft dough carrier base comprises flour, an emulsifier, a starch, an oil, a softening agent, and water.

2. A method of treating atopic dermatitis in a mammal comprising administering the composition of claim 1 to the mammal.

\* \* \* \* \*